United States Patent [19]

Mochizuki et al.

[11] Patent Number: 5,152,294
[45] Date of Patent: Oct. 6, 1992

[54] THREE-DIMENSIONAL ULTRASONIC SCANNER

[75] Inventors: Takashi Mochizuki; Syohgo Iijima, both of Mitaka, Japan

[73] Assignee: Aloka Co., Ltd., Mitaka, Japan

[21] Appl. No.: 627,850

[22] Filed: Dec. 14, 1990

[30] Foreign Application Priority Data

Dec. 14, 1989 [JP] Japan .................................. 1-324957
Sep. 14, 1990 [JP] Japan .................................. 2-245002

[51] Int. Cl.⁵ ............................................. A61B 8/00
[52] U.S. Cl. .............................. 128/662.03; 128/916; 128/660.09; 128/660.10; 128/661.01
[58] Field of Search .................. 128/660.09, 660.10, 128/661.01, 662.03, 916

[56] References Cited

U.S. PATENT DOCUMENTS

| | | | |
|---|---|---|---|
| 4,186,747 | 2/1980 | Iinuma | 128/660.08 |
| 4,271,706 | 6/1981 | Ledley | 128/916 |
| 4,282,879 | 8/1981 | Kunii et al. | 128/660.09 |
| 4,431,007 | 2/1984 | Amazeen et al. | 128/661.01 |
| 4,637,256 | 1/1987 | Sugiyama et al. | 128/660.09 |
| 4,913,158 | 4/1990 | Kikuchi et al. | 128/660.10 |
| 4,932,414 | 6/1990 | Coleman | 128/660.09 |

FOREIGN PATENT DOCUMENTS

| | | | |
|---|---|---|---|
| 2826828 | 7/1979 | Fed. Rep. of Germany | 128/660.09 |
| 3405537 | 8/1985 | Fed. Rep. of Germany | 128/660.09 |
| 233724 | 8/1987 | Japan | 128/660.09 |
| 390311 | 10/1990 | Japan | 128/660.09 |

Primary Examiner—William E. Kamm
Assistant Examiner—George Manuel
Attorney, Agent, or Firm—Fish & Richardson

[57] ABSTRACT

A three-dimensional ultrasonic scanner for acquiring data concerning a three-dimensional area within a living body to be examined. In the inside of a scanner case is encased an array transducer unit. Further, at the end bottom portion of the transducer unit there is provided an array transducer composed of a plurality of transducer elements arranged in line one after another. The electronic scanning of this array transducer produces a two-dimensional scanning plane. In addition, a swinging mechanism is provided for mechanically swinging the transducer unit in a direction normal to the arrangement direction of the transducer elements. This mechanical swing movement of the transducer unit shifts the two-dimensional scanning plane to a direction normal thereto, thereby forming a three-dimensional data acquisition area within the living body. Here, a swing angle of the transducer unit is detected by an angle detector.

17 Claims, 5 Drawing Sheets

THREE-DIMENSIONAL ULTRASONIC SCANNER

BACKGROUND OF THE INVENTION

1. Field of the Invention

The present invention relates to an ultrasonic scanner for transmitting/receiving ultrasonic beams and, more particularly, to an ultrasonic scanner capable of acquiring three-dimensional data concerning objects within a living body to be examined for a three-dimensional medical diagnosis use.

2. Description of the Related Arts

In the medical field, the technique of ultrasonic diagnosis has been widely utilized. Such a medical diagnosis is performed by the use of an ultrasonic diagnostic apparatus composed of a mainframe of an ultrasonic diagnostic apparatus and a scanner including an array transducer. In practice, the diagnostic apparatus transmits ultrasonic beams and receives reflected echoes from objects in the living body by means of an ultrasonic scanner being in contact with a skin of the body, and thus acquired echo data are analyzed and processed by the mainframe of the diagnostic apparatus, so that the information of cross-sectional layer image and blood flow velocity, etc., are visually displayed in the form of a dynamic image.

Figure 1:
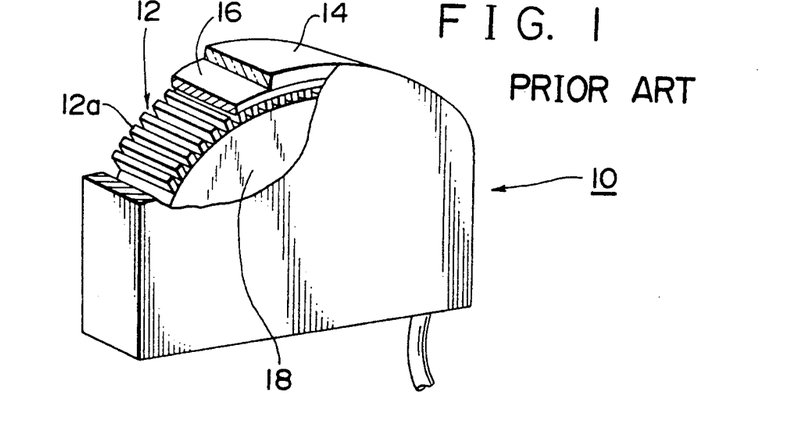
FIG. 1 is a partially broken away perspective view of a conventional scanner.

Prior to describing in detail the structure of the ultrasonic scanner according to this invention, an explanation of a conventionally used convex type scanner will be made with reference to FIG. 1.

In accordance with this conventional ultrasonic scanner denoted with a numeral 10, an array transducer 12 disposed inside of a convex-shaped end portion of the scanner effects the transmission and reception of an ultrasonic beam. As is apparent from the drawing, this array transducer 12 is composed of a plurality of transducer elements 12a arranged along the end surface of the convex-shaped scanner 10.

At the curved end surface of the scanner 10 is disposed an acoustic lens 14 for focusing ultrasonic beam, and a matching layer 16 for matching acoustic impedance is disposed between the acoustic lens 14 and the array transducer 12. In addition, a backing layer 18 is disposed behind of the array transducer 12 for absorbing unnecessary ultrasonic waves.

With such a structure, the application of a drive signal to each transducer element 12a causes the ultrasonic beam to be transmitted in a direction normal to the upper surface of the element 12a. With this result, it becomes possible to acquire data concerning a fan-shaped two-dimensional area.

However, in accordance with the conventional ultrasonic scanner, it is hard to obtain information other than echo data concerning a two-dimensional area with the scanner stationary. To observe an affected organ within a living body three-dimensionally, it is necessary to intentionally move the position, or incline the angle, of the scanner by a manual operation.

When the scanner is moved or inclined by manual operation, it is highly difficult to observe the target organ at the optimum position and with the optimum angle, and also the data acquisition is disadvantageously disturbed. For such a reason, there has been a demand in a medical service field for an ultrasonic scanner capable of securely and accurately acquiring echo data concerning a three-dimensional area within the living body.

Further, according to advances in image processing techniques, it is now proceeding the development of an apparatus for visually and three-dimensionally displaying an image of an target in a three-dimensionally specified area within the living body. Even in the development of such apparatus, there has been expected the introduction of the ultrasonic scanner capable of acquiring three-dimensional information of the echo data.

This invention aims to solve foregoing drawbacks with the prior arts, and the object of the invention is to provide a three-dimensional ultrasonic scanner which is capable of acquiring data concerning a three-dimensional area within the body by specifying a position in three dimension without inclining the angle, or moving the position, of the scanner manually and intentionally.

SUMMARY OF THE INVENTION

To this end, according to one aspect of the present invention, there is provided a three-dimensional ultrasonic scanner comprising: a transducer unit including an array transducer at the end portion thereof; a swing mechanism for swinging the transducer unit; and an angle detector for detecting a swing angle of the transducer unit.

With this structure, the transducer unit is swung in a direction normal to a direction in which a plurality of transducer elements are arranged, and the angle formed by this swing operation is concurrently detected by the angle detector.

In consequence, since the data acquisition can be realized in a three-dimensional area by mechanically swinging the two-dimensional data acquisition plane constituted by the scanning of the array transducer, accurate and stable data acquisition can be realized independent of any manual and intentional operation.

As another advantage of the invention is that since the three-dimensional position of the echo data is determined by an address of the transducer element to be driven and the swing angle, it becomes possible to supply the mainframe of the ultrasonic diagnostic apparatus with information as to the swing angle indispensable for executing the processing of three-dimensional images.

Further advantage of this invention is that it is possible to propagate acoustic energy between the transducer unit and the skin surface of the living body without passing through air by providing the medium bath within the scanner case.

The foregoing object, features and advantages of the invention will be apparent from the following description of preferred embodiments of the invention, as illustrated in the accompanying drawings.

DETAILED DESCRIPTION OF THE PREFERRED EMBODIMENTS

Preferred embodiments of the present invention will now be described with reference to the accompanying drawings.

Figure 2:
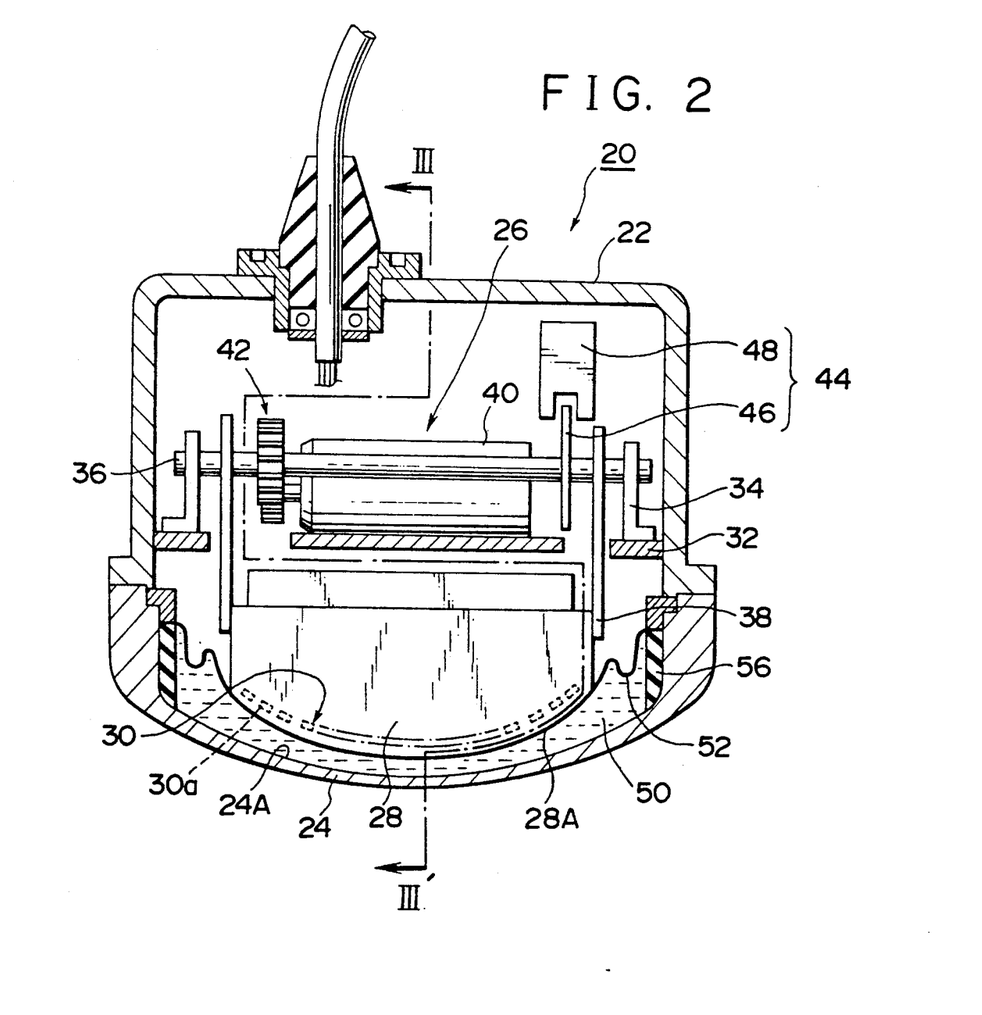
FIG. 2 is a front sectional view of the three-dimensional scanner in accordance with one preferred embodiment of the invention.
Figure 3:
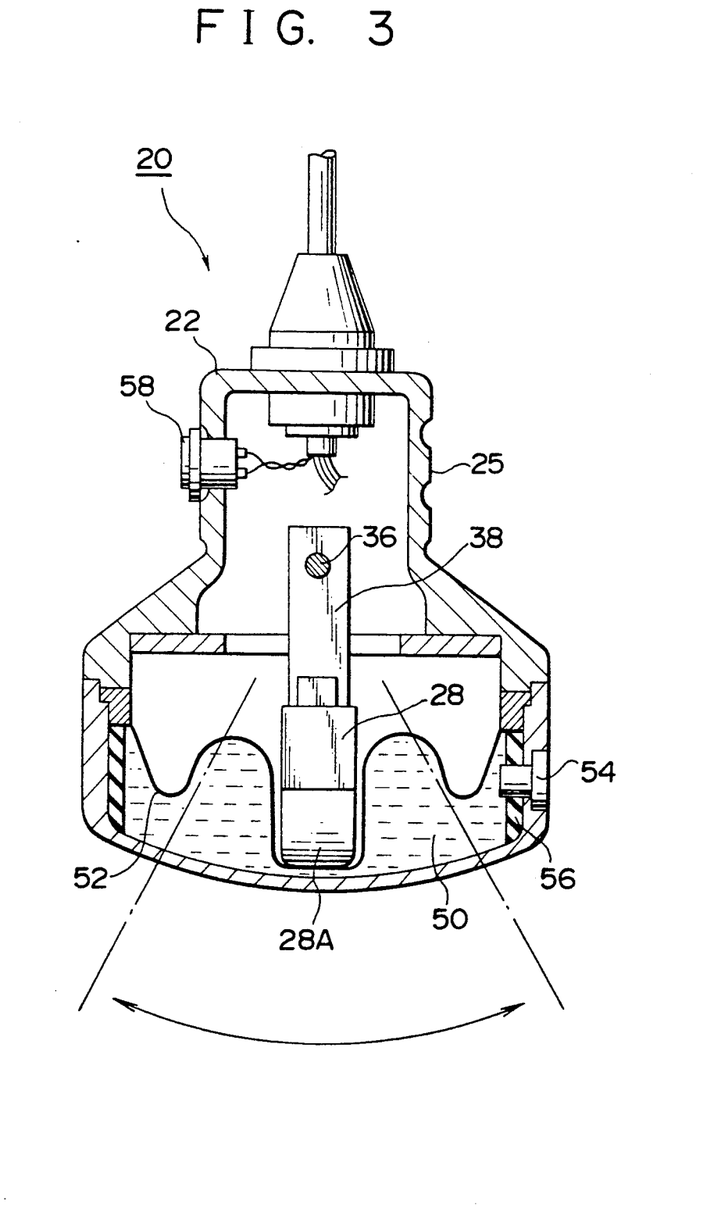
FIG. 3 is a sectional view of the scanner shown in FIG. 2, taken along a dash-and-one-dot line III—III' shown therein.

FIG. 2 is a front sectional view of the three-dimensional scanner in accordance with one preferred embodiment of the invention. FIG. 3 is a sectional view of the scanner shown in FIG. 2, taken along a dash-and-one-dot line III—III' shown therein.

In FIG. 2, a scanner case 22 in which an ultrasonic scanner 20 is encased has a contact wall 24, which constitutes a bottom part of wall and is formed in a rather smooth convex shape not to provide discomfort to the patient when contacting the scanner with the skin of the patient. Meanwhile, as can be seen from FIG. 3, a grip portion 25, which constitutes the upper portion of the scanner case 22, has a thickness thinner in side elevation view than that of the lower portion of the case 22 so as to provide an easy gripping possibility.

In the inside of the scanner case 22, there is provided a transducer unit 28 which is subject to swing action of a swing mechanism 26.

As shown in FIG. 2, the transducer unit 28 is shaped at its lower bottom end into a convex, and an array transducer 30 is arranged inside of the end portion in parallel with the convex-shape periphery. The array transducer 30 is composed of a plurality of transducer elements 30a which are arranged in parallel with the convex-shape end surface 28A of transducer unit 28.

Although not shown, an acoustic lens is disposed at the convex end surface 28A for the purpose of preventing undesired and disturbing propagation of ultrasonic waves. Further, there is provided a matching layer between the acoustic lens and the array transducer 30, for proper matching of the acoustic impedance. Still further, a backing layer is provided at the rear of the array transducer 30.

Next, the structure and operation of a swing mechanism 26 for effecting a swing operation of the transducer unit 28 will be described hereunder.

In the interior of the scanner case 22, there is provided a base 32 for dividing the inside space substantially into two parts. A pair of oppositely provided bearing members 34 are mounted on the base 32 for rotatably mounting a support shaft 36.

The transducer unit 28 is suspended at the lower ends of two supporting arms 38, while the upper ends of these arms 38 are securely fixed to the support shaft 36.

Thus, as clearly be seen from FIG. 2, the transducer unit 28 is suspended with mated to the support shaft 36 in such a position as directing its transmitting/receiving surface 28A downwards or more specifically towards the non-illustrated living body to be examined.

Upon the base 32 is disposed a motor, or a drive source, for swinging the transducer unit 28 around the support shaft 36. In order to transmit the drive energy of the motor 40 to the support shaft 36, there are provided a gear section 42 composed of a plurality of gears between the motor 40 and the support shaft 36.

As mentioned above, the swing mechanism 26 comprises the motor 40, the gear section 42, the support shaft 36 and the suspension arms 38.

With this mechanism, when the motor 40 is energized, the transducer unit 28 can be swung around the support shaft 36 in a direction normal to the arrangement direction of the transducer elements 30a.

Next, the operation of an angle detector 44 for detecting a swing angle of the transducer unit 28 will be explained hereunder.

This angle detector 44 comprises a slit disc 46 fixed on the support shaft 36 and a photointerrupter 48, the one end of which emits light to produce a light path while the other end of which counts the number of times a given light has passed through the slit disc 46.

Figure 7:
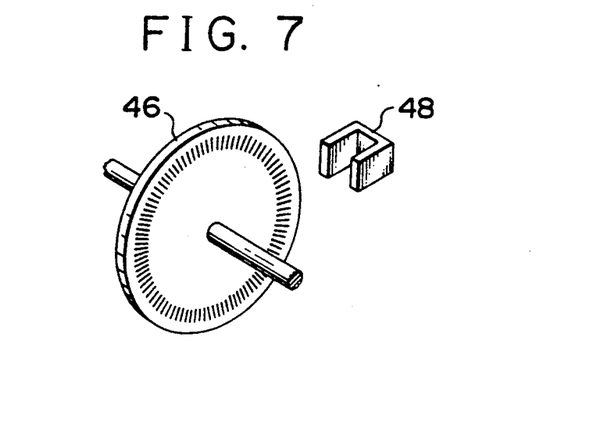
FIG. 7 is an exploded perspective view of an angle detector adopted in the three-dimensional ultrasonic scanner embodying the present invention.

This angle detector 44 is further illustrated in an exploded perspective view of FIG. 7 more specifically.

It will be easily understood that by means of such angle detector 44, the swing angle of the transducer unit 28 can be constantly detected. Further, if necessary, thus obtained swing angle information could be utilized for feedback control of the swing movement. As a matter of course, the structure of the angle detector 44 cannot be limited to the aforementioned one but may be modified into other forms.

Next, an explanation will be given to a coupling medium bath 50 shown in FIG. 2.

As illustrated, the coupling medium bath 50 is disposed in the inner bottom part of the scanner case 22; or more specifically, the bath 50 is formed in a space between a partition membrane 52 and a concave inner bottom surface 24A, being filled with an acoustic energy propagation medium.

The outer periphery of the partition membrane 52 is hermetically attached to the inner side wall of the scanner case 22, and a substantial middle portion of the membrane 52 is adhered to the overall surface of the ultrasonic beam transmitting/receiving end surface 28A.

This partition membrane 52 has a somewhat looseness as shown in FIG. 3 for allowing the swing movement of the transducer unit 28.

As a result, as has been mentioned, the space between the partition membrane 52 and the concave inner bottom surface 24A is hermetically sealed, and the acoustic impedance matching is maintained by interposing the acoustic energy propagation medium therebetween regardless of what swing angle the transducer unit 18 takes and what position the scanner is located in.

Specifically, as is well known, an ultrasonic beam causes considerable reflection at the boundary surface between materials having different acoustic impedances. Therefore, with the interposition of such a coupling medium bath 50, there is secured the acoustic propagation of ultrasonic waves emanated from the beam transmitting/receiving end surface 28A of the transducer unit 28 without air on the way of beam propagation path.

The acoustic energy propagation medium may be poured into the bath 50 through an inlet 54 shown in FIG. 3. Alternatively, this medium may be replaced with any liquid having an acoustic impedance similar to that within the living body, for example, water, oil, or the like.

Figure 4:
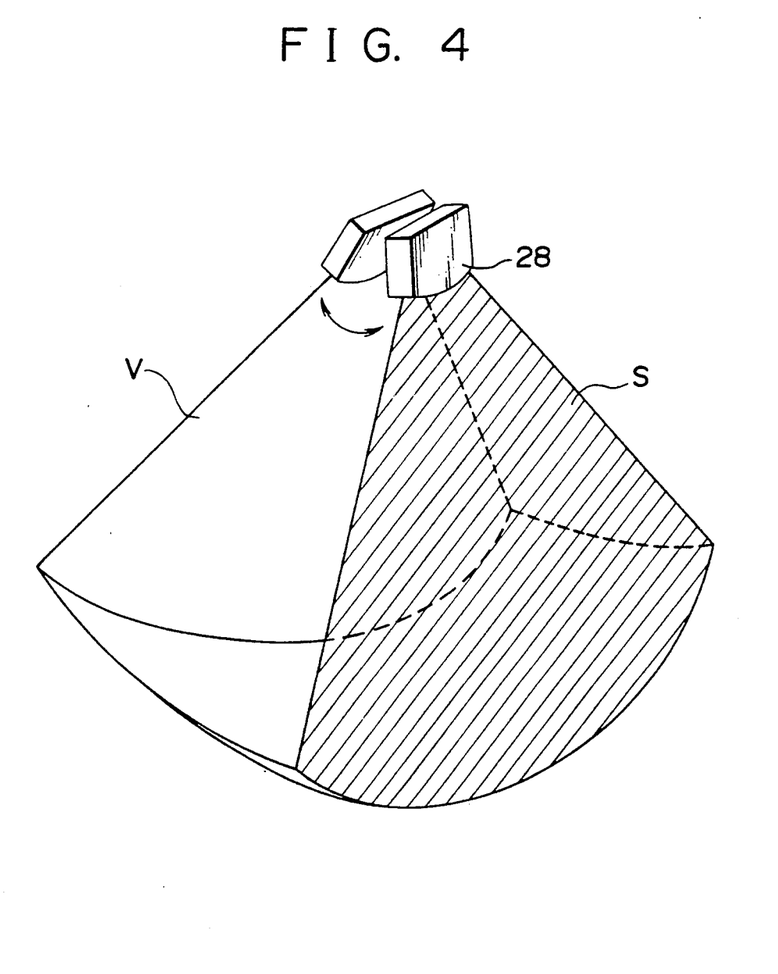
FIG. 4 is a schematic perspective view illustrating specifically the three-dimensional data acquisition area as "V"

Referring to FIG. 4, a description will now be given to a data acquisition area of three-dimension produced by the ultrasonic scanner 20 according to this invention.

In FIGS. 2 and 4, a scanning plane "S" of a fan-shaped two dimensional scanning area shown as shaded is obtained by an electronic scanning of the ultrasonic beam. More specifically, this electronic scanning plane "S" has been realized in such a way that a plurality of transducer elements 30a were sequentially driven one by one or simultaneously in plural.

As was described hereinbefore, by the use of the conventional ultrasonic scanner, only two-dimensional scanning plane "S" is obtained as a data acquisition area. According to this invention, the swing movement of the transducer unit 28 can be realized in a direction normal to the arrangement direction of the transducer elements 30a, or a direction normal to the scanning plane S, by means of the swing mechanism 26, whereby it becomes possible to acquire echo data concerning the data acquisition area V shown in FIG. 4.

More in detail, first, echo data concerning a scanning plane S are acquired at a given angle, and then another echo data concerning the scanning plane S are acquired after the scanning plane S has been advanced at a minute swing angle. Through the successive repetition of the series of data acquisition operations, it is possible to realize data acquisition of all information concerning the data acquisition area V.

In addition, since the swing angle of each scanning plane S is constantly detected by the angle detector 44, it is possible to execute the data acquisition by obtaining the accurate positional relationship among scanning planes.

Next, there is explained a multiple reflection phenomenon of ultrasonic waves caused between the beam transmitting/receiving surface 28A of the transducer unit 28 and the concave inner bottom surface 24A.

Figure 5:
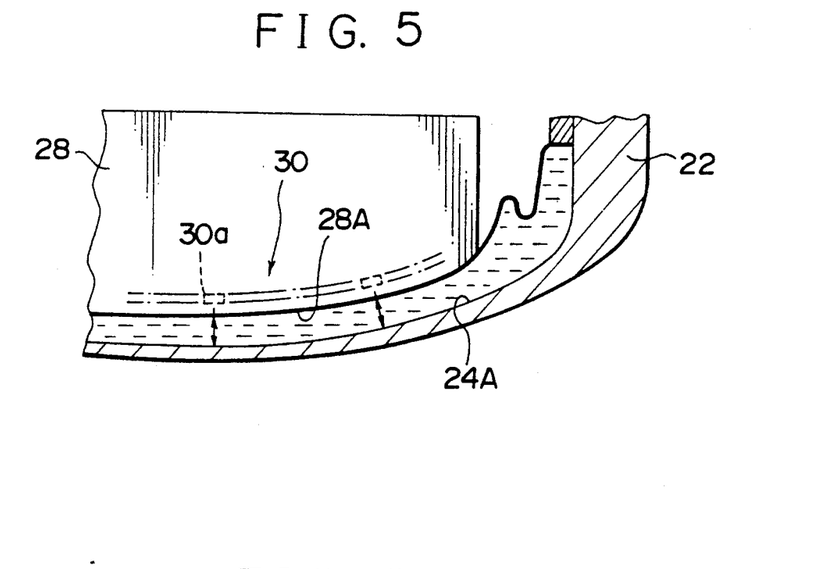
FIG. 5 is a partially cutaway enlarged view of a scanner including the multiple reflection of ultrasonic waves.

FIG. 5 shows an exemplary phenomenon of the multiple reflection of ultrasonic waves for comparative explanation.

As is obvious from FIG. 5, in case both the concave inner bottom surface 24A and the beam transmitting/receiving surface 28A have almost same curvature in the arrangement direction of the transducer elements, a part of ultrasonic waves emanated from the transducer element 30a is once reflected by the concave inner bottom surface 24A and is further reflected by the beam transmitting/receiving surface 28A. The repetition of such reflection phenomenon causes the multiple reflection of ultrasonic waves. As a result of this, the occurrence of noises in the acquired echo data causes the mainframe of the ultrasonic diagnostic apparatus to produce an ambiguous image.

Figure 6:
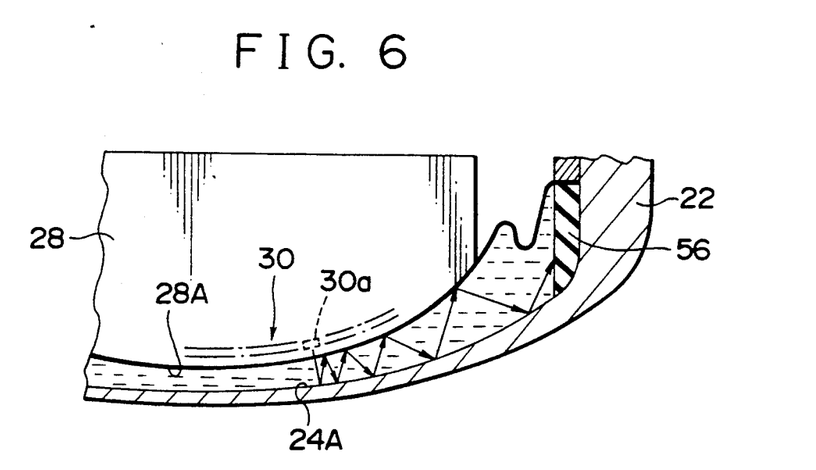
FIG. 6 is a partially cutaway enlarged view of the three-dimensional ultrasonic scanner illustrating the absorption of the unnecessary multi-reflected ultrasonic waves by means of absorption material employed in this scanner.

To avoid this problem, in accordance with the three-dimensional ultrasonic scanner, the shapes of the concave inner bottom surface 24A and the beam transmitting/receiving surface 28A are designed, so that the curvature of the former becomes smaller than that of the latter. Namely, the shapes of the concave inner bottom surface 24A and the beam transmitting/receiving surface 28A are selected in such a manner that the radius of curvature of the concave inner bottom surface 24A is larger than that of the surface 28A.

Moreover, upon the inner side wall of the coupling medium bath 50 is disposed an absorbing material 56 of ultrasonic waves.

With this structure, as shown in FIG. 6, a part of ultrasonic waves emanated from the transducer element 30a is reflected by the concave inner bottom surface 24A and is further reflected by the beam transmitting/receiving surface 28A, and thus reflected wave is further reflected between two surfaces successively and lead to the periphery of the coupling medium bath 50. Finally, the reflected wave is absorbed by the ultrasonic wave absorbing material 56.

Accordingly, with this structure, the multiple reflection of ultrasonic waves is effectively eliminated, whereby it becomes possible to suppress the occurrence of noise in the acquired data as least as possible.

As a preferred embodiment of the invention, the radius of curvature of the concave inner bottom surface 24A is 100 mm or so, while that of the beam transmitting/receiving surface 28A is 60 mm or so. It should be noted that the same result may be obtained if only the radius of curvature of the concave inner bottom surface 24A is larger than that of the beam transmitting/receiving surface 28A. On this point, in accordance with the experiment, it is recognized that, with this aforementioned structure, the multiple reflection of the waves was successfully eliminated with high efficiency.

In this embodiment, silicon rubber is used for the foregoing ultrasonic wave absorbing material 56. Furthermore, in accordance with this embodiment, the ultrasonic wave absorbing material 56 is disposed along the inner whole circumference of the lower part of the scanner case 22 in order to eliminate unnecessary ultrasonic waves by absorption as much as possible. Incidentally, if the difference between the radii of curvature of the concave inner bottom surface 24A and the beam transmitting/receiving surface 28A becomes excessively large, the beam emanated from the beam transmitting/receiving surface 28A may be reflected too much by the concave inner bottom surface 24A. Therefore, it will be preferable to select the difference value of the two radii within the range suitable for the practical use.

An operation switch 58 will now be described with reference to FIG. 3.

As shown in FIG. 3, the operation switch 58 is provided on a grip portion 25. This operation switch 58 serves to start and stop the data acquisition action, and the operation of the switch 58 by the operator enables the data acquisition operation to be performed with ease. As an alteration, it may be possible to add further functions, such as a momentary suspension of swing movement or the like.

Thus, in accordance with the three-dimensional ultrasonic scanner embodying the present invention, it is possible to acquire data concerning a three-dimensional area within the living body with the ultrasonic wave scanner 20 kept in contact with the surface of the living body and without inclining or moving the scanner itself.

Further it should be understood that it becomes possible to execute the acquisition of highly accurate echo data with the appropriate propagation of ultrasonic beam realized by the adoption of the coupling medium bath 50 and the ultrasonic wave absorbing material 56.

A description of a backlash of the gear section will be given hereinbelow.

To suppress the backlash at the gear section 42, it will be preferable to exert compulsive force upon the transducer unit 28 in either of the swing directions by means of the spring, for example.

Further, as an example for reference, there will be described the operation of one exemplary ultrasonic diagnostic apparatus capable of displaying three-dimensional images adopting the three-dimensional scanner in accordance with the present invention.

Figure 8:
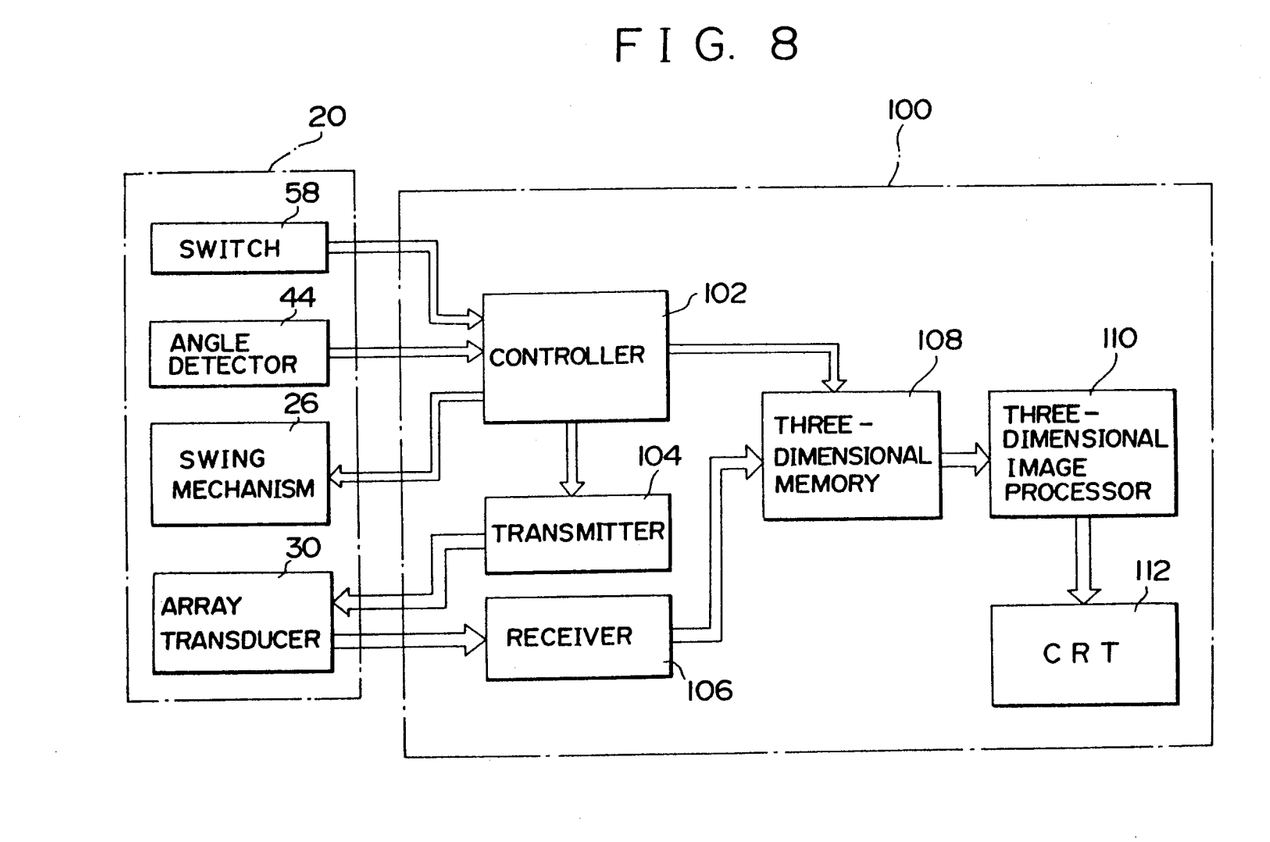
FIG. 8 is a block diagram of the three-dimensional ultrasonic scanner in accordance with one embodiment of the present invention.

The ultrasonic diagnostic apparatus shown in FIG. 8 comprises the three-dimensional ultrasonic scanner 20 and a mainframe 100 of the ultrasonic diagnostic apparatus for processing data acquired and displaying images obtained therefrom.

A controller 102 incorporated in the mainframe 100 controls read/write of data into a three-dimensional memory 108 described later as well as controls a swing mechanism 26 of the scanner 20.

At the controller 102 is supplied an angle detection signal from the angle detector 44 as well as is inputted an operation signal from the operation switch 58. The controller 102 controls the swing mechanism 26 in response to these signals. A transmitter 104 serves for supplying a transmission signal to the array transducer 30, and the operation thereof is controlled by the controller 102.

A receiving signal from the array transducer 30 is inputted to a receiver 106. This receiver 106 performs amplification and detection of the receiving signal, and a processed signal is then delivered to the three-dimensional memory 108.

This three-dimensional memory 108 serves for storing echo data concerning the three-dimensional data acquisition area V shown in FIG. 4 in such a manner that the three-dimensional position of the echo data corresponds to each address in the memory. Writing of the echo data in the memory is controlled by the controller 102 in response to the angle signal from the angle detector 44.

The echo data stored in the three-dimensional data memory 108 are successively read out and inputted into a three-dimensional image processor 110. This three-dimensional image processor 110 serves for executing the image processing for stereographically displaying images on the basis of the echo data concerning the three-dimensional area within the living body to be examined.

Thus formed three-dimensional images are in consequence transferred to a CRT 112, and is displayed in image.

Therefore, by the use of the ultrasonic diagnostic apparatus embodying the present invention, it can be seen that it is possible to observe the state of target objects such as affected organs stereographically from the images obtained, thereby improving the accuracy of the medical diagnosis.

It will be apparent that many modifications and variations may be effected without departing from the scope of the novel concepts and teachings of the present invention.

What is claimed is:

1. A three-dimensional ultrasonic scanner, comprising:
    a scanner case;
    a transducer unit encased in said scanner case and having an array transducer comprising a plurality of transducer elements disposed at an end portion thereof;
    swing means for swinging said transducer unit within said scanner case in a direction normal to a scanning plane produced by the plurality of transducer elements; and
    angle detection means for detecting a swing angle of the transducer unit relative to the scanner case.

2. A three-dimensional ultrasonic scanner as claimed in claim 1, further comprising acoustic energy coupling means disposed between the end portion of the transducer unit and an inner bottom surface of the scanner case.

3. A three-dimensional ultrasonic scanner as claimed in claim 2, wherein said acoustic energy coupling means comprises a flexible partition membrane hermetically attached at a peripheral portion thereof to inner side wall portions of the scanner case so as to define a sealed space between the partition membrane, the inner side wall portions and the inner bottom surface of the scanner case, and wherein said sealed space is filled with an acoustic energy propagation medium.

4. A three-dimensional ultrasonic scanner as claimed in claim 3, wherein the end portion of the transducer unit is attached to a top central portion of the flexible partition membrane, and wherein the flexible partition membrane is sufficiently loose to allow the transducer unit to swing within the scanner case.

5. A three-dimensional ultrasonic scanner as claimed in claim 3, further comprising inlet means provided in the case for accessing the sealed space.

6. A three-dimensional ultrasonic scanner as claimed in claim 1, wherein the end portion of the transducer unit comprises a convex end surface, and wherein said plurality of transducer elements are arranged in parallel along the convex surface.

7. A three-dimensional ultrasonic scanner as claimed in claim 6, wherein the inner bottom surface of the scanner case has a concave shape.

8. A three-dimensional ultrasonic scanner as claimed in claim 7, wherein the curvature of the inner bottom surface of the scanner case is smaller than the curvature of the convex end surface of the transducer unit.

9. A three-dimensional ultrasonic scanner as claimed in claim 8, further comprising means for absorbing ultrasonic waves disposed on inner side wall portions of the scanner case.

10. A three-dimensional ultrasonic scanner as claimed in claim 9, wherein said means for absorbing ultrasonic waves comprises silicon rubber.

11. A three-dimensional ultrasonic scanner as claimed in claim 9, further comprising an operation switch provided on an upper portion of the scanner case for effecting a data acquisition operation.

12. A three-dimensional ultrasonic scanner as claimed in claim 1, wherein said swing means comprises at least one drive motor and gear means comprising a plurality of gears.

13. A three-dimensional ultrasonic scanner as claimed in claim 12, wherein said transducer unit is suspended from a supporting shaft disposed across an interior portion of the scanner case by means of at least one suspension arm mounted to the transducer unit, and wherein the supporting shaft is driven by said drive motor.

14. A three-dimensional ultrasonic scanner, comprising:
    a scanner case;
    a transducer unit encased in said scanner case and having an array transducer comprising a plurality of transducer elements disposed at an end portion thereof;
    acoustic energy propagation means disposed between the end portion of the transducer unit and an inner bottom surface of the scanner case, said means comprising a partition membrane hermetically attached at a peripheral portion thereof to inner side wall portions of the scanner case and attached at a top central portion thereof to the end portion of the transducer unit so as to define a sealed space between the partition membrane, the inner side wall portions and the inner bottom surface of the scanner case, and wherein said sealed space is filled with an acoustic energy propagation medium.

15. A three-dimensional ultrasonic scanner, comprising:
a scanner case having a concave inner bottom surface of a first curvature;
a transducer unit encased in said scanner case and having an end portion defining a convex transmitting/receiving surface having a second curvature, said transducer unit including an array transducer comprising a plurality of transducer elements arranged along said convex transmitting/receiving surface;
wherein said first curvature is larger than said second curvature and wherein said second curvature becomes gradually smaller from a central portion of the inner bottom surface to a peripheral portion thereof.

16. A three-dimensional ultrasonic scanner as claimed in claim 15, further comprising acoustic energy propagation means disposed between the transmitting/receiving surface of the transducer unit and the inner bottom surface of the scanner case.

17. A three-dimensional ultrasonic scanner as claimed in claim 16, wherein said acoustic energy propagation means comprises a partition membrane hermetically attached at a peripheral portion thereof to inner side surfaces of the scanner case and attached at a top central portion thereof to the transmitting/receiving surface of the transducer unit so as to define a sealed space between the partition membrane, the inner side surfaces of the scanner case, and the bottom surface of the scanner case, wherein said sealed space is filled with an acoustic energy propagation medium.

* * * * *